United States Patent

Huber et al.

[11] Patent Number: 5,811,188
[45] Date of Patent: Sep. 22, 1998

[54] PHOSPHORUS-MODIFIED EPOXY RESINS, PROCESSES FOR THEIR PREPARATION AND THEIR USE

[75] Inventors: Jürgen Huber, Erlangen; Heinrich Kapitza, Fürth; Hans-Jerg Kleiner, Kronberg; Wolfgang Rogler, Möhrendorf, all of Germany

[73] Assignees: Siemens Aktiengesellschaft, München; Aventis Research & Technologies GmbH & Co. KG, Frankfurt am Main, both of Germany

[21] Appl. No.: 776,860

[22] PCT Filed: Jul. 26, 1995

[86] PCT No.: PCT/EP96/02965

§ 371 Date: Feb. 28, 1997

§ 102(e) Date: Feb. 28, 1997

[87] PCT Pub. No.: WO96/04327

PCT Pub. Date: Feb. 15, 1996

[30] Foreign Application Priority Data

Aug. 3, 1994 [DE] Germany ............. 44 27 456.4

[51] Int. Cl.⁶ ............. C08G 59/14; C08L 63/00
[52] U.S. Cl. ............. 428/413; 428/415; 428/417; 428/901; 525/523; 525/525; 528/103; 528/108; 528/361; 528/398; 528/400; 427/386
[58] Field of Search ............. 525/523, 525; 528/108, 361, 398, 400, 103; 428/413, 415, 417, 901; 427/386

[56] References Cited

U.S. PATENT DOCUMENTS

| | | | |
|---|---|---|---|
| 4,164,487 | 8/1979 | Martin | 528/99 |
| 4,195,035 | 3/1980 | Kleiner et al. | 562/878 |
| 4,289,812 | 9/1981 | Martin | 427/379 |
| 4,783,345 | 11/1988 | Kleeberg et al. | 427/96 |
| 4,952,646 | 8/1990 | Weil et al. | 528/108 |
| 5,319,138 | 6/1994 | Roscher et al. | 562/878 |
| 5,364,893 | 11/1994 | von Gentzkow et al. | 523/429 |
| 5,587,243 | 12/1996 | Von Gentzkow et al. | 428/413 |

FOREIGN PATENT DOCUMENTS

| | | |
|---|---|---|
| 2158361 | 9/1994 | Canada . |
| 0 004 323 | 10/1979 | European Pat. Off. . |
| 0 274 646 | 7/1988 | European Pat. Off. . |
| 0 384 939 | 9/1990 | European Pat. Off. . |
| 1503429 | 11/1967 | France ............. 528/108 |
| 1 287 312 | 9/1969 | Germany . |
| 2 129 583 | 12/1972 | Germany . |
| 27 57 733 | 7/1978 | Germany . |
| 27 43 680 | 4/1979 | Germany . |
| 27 58 580 | 7/1979 | Germany . |
| 43 08 185 | 9/1994 | Germany . |
| 4308185 | 9/1994 | Germany ............. 528/108 |

OTHER PUBLICATIONS

Appendix I, Synthesis of Epoxy Resins, pp. 198–207.
Novel Thermosetting Epoxy Resins Based on Pentaerythritol, J. M. Jordan, pp. 1–15.
Handbook of Epoxy Resins, Chapter 2, Synthesis of Glycidyl–type epoxy resin, pp. 2–1–2–33.
K. Sasse: Phosphonsäuren und Derivate, pp. 612, 613.
Die Angewandte Makromolekulare Chemie 44 (1975) pp. 151–163 Nr. 679 *Thermisches Verhalten von Mono–, Bis–und Poly–2–oxazolidinonen*.
Polyadditionscharze, pp.174–194.
International Plastics Flammability, 5.2 The most important fire retardant plastics, pp. 53–60.
Epoxies and Silicones, Adducts of Cyclic Urea Derivatives and Dialkyl Phosphites, pp. 119–131.

*Primary Examiner*—Frederick Krass

[57] ABSTRACT

The present invention relates to phosphorus-modified epoxy resins of the formulae (I) and/or (II)

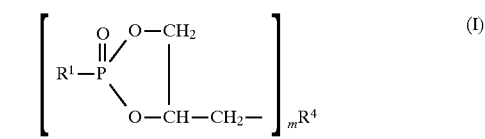

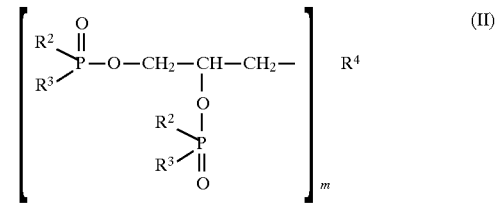

The invention furthermore relates to a process for the preparation of these phosphorus-modified epoxy resins and to their use for the production of shaped articles, coatings or laminates.

16 Claims, No Drawings

PHOSPHORUS-MODIFIED EPOXY RESINS, PROCESSES FOR THEIR PREPARATION AND THEIR USE

The present invention relates to novel phosphorus-modified epoxy resins, a process for their preparation and their use. The novel phosphorus-modified epoxy resins are distinguished as flame retardant additives having very processing-friendly properties.

Epoxy resins are widely employed nowadays for the production of reactive resin molded materials and coatings having a high level of thermal, mechanical and electrical properties and for the production of laminates. The low molecular weight or oligomeric starting components can be reacted to high-quality thermosetting materials using the most diverse hardeners, such as, for example, carboxylic acid anhydrides, amines, phenols or isocyanates, or by ionic polymerization. The processing properties of epoxy resins is another of their advantages. In the starting state they are low molecular weight or oligomeric and have a low viscosity at processing temperatures. They are therefore particularly suitable for sealing complex electrical and electronic components and for soaking and impregnating processes. They have adequate pot lives in the presence of suitable reaction accelerators. They can also be filled to a high degree with customary inorganic inert fillers.

In order to protect persons affected in the event of a fire or a malfunction and in order to assure functioning of electrical and electronic equipment is maintained over a certain period of time, epoxy resin molded materials (cured epoxy resins) are often required to have flame resistance in electrical engineering. This means that epoxy resin molded materials must be self-extinguishing and should not transmit the fire. The detailed requirements are given in the standards relating to the particular product. For epoxy resin molded materials employed in electronics and electrical engineering, combustibility testing in accordance with UL 94V mainly applies here.

A summary of the possible methods for rendering epoxy resins flame resistant is to be found in the literature (for example Troitzsch, J., "International Plastics Flammability Handbook", 2nd Edition, Carl Hanser Verlag, Munich, 1990; Yehaskel, A., "Fire and Flame Retardant Polymers", Noyes Data Corporation, New Jersey, USA, 1979).

Epoxy resin molded materials are currently in general provided with a flame resistant finish by means of halogen-containing, specifically bromine-containing, aromatic components. The materials are usually molded materials which comprise intercalation components, for example fillers or glass fabric, and often comprise antimony trioxide as a synergist. The problem here is that in the event of a malfunction, decomposition products which are corrosive and under unfavorable conditions are ecologically or toxicologically unacceptable are formed owing to smouldering or combustion. There must be a considerable technical expenditure for hazard-free disposal by combustion.

There is therefore a considerable demand for epoxy resins which achieve the low combustibility required in the standards without the addition of halogenated components.

The use of organic phosphorus compounds has proven to be an effective way of achieving flame resistance in resinous substrates. Attempts have therefore already been made to modify epoxy resins with additives based on phosphoric acid esters such as, for example, triphenyl phosphate (DE 1 287 312). However, these compounds migrate out of the molded materials to the surface, especially at elevated temperature, affecting the dielectric properties and leading to E corrosion.

The object of the invention was therefore to provide novel phosphorus-containing additives for epoxy resins which, in addition to flame resistance, also have high storage stability, allow variations in the phosphorus content, are simple and inexpensive to prepare and above all are also suitable for use in electronics and electrical engineering where high filler contents are customary.

The present invention thus relates to novel phosphorus-modified epoxy resins of the formula (I) and/or of the formula (II)

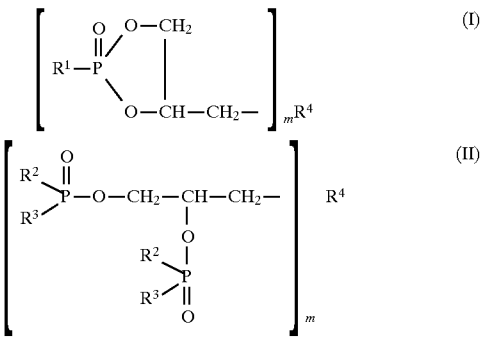

in which:
  $R^1$, $R^2$ and $R^3$ independently of one another are a hydrocarbon radical having 1 to 20 carbon atoms, preferably 1 to 10 carbon atoms,
  $R^4$ is the radical, reduced by glycidyl groups, of a polyepoxide compound, preferably a diepoxide compound, containing glycidyl groups and
  m is an integer from 2 to 6, preferably 2 to 4, and in particular 2.

The invention furthermore relates to a process for the preparation of such phosphorus-modified epoxy resins and to their use for the production of shaped articles, coatings and laminates (composite materials) and to these objects themselves.

The phosphorus-modified epoxy resins according to the invention in general have an average molecular weight $\overline{M}_n$ (number-average; determined by means of gel chromatography; polystyrene standard) of up to about 10 000, preferably about 200 to 5 000, and in particular 400 to 2 000.

In the above formulae (I) and (II), $R^1$, $R^2$ and $R^3$ are preferably a hydrocarbon radical which has an aliphatic and/or aromatic character and can be interrupted by hetero atoms or hetero atom groups, in particular a saturated or unsaturated, straight-chain or branched aliphatic radical, such as alkyl, alkenyl or cycloalkyl having preferably 1 to 8 carbon atoms, in particular 1 to 4 carbon atoms, such as methyl, ethyl, n- or i-propyl or n-, i- or tert-butyl. These radicals furthermore can also be an aryl or an aralkyl radical, such as phenyl or naphthyl which are unsubstituted or substituted by preferably 1 to 3 alkyl radicals having 1 to 6 carbon atoms, or such as phenylalkyl having 1 to 6 carbon atoms in the alkyl radical, for example benzyl.

$R^4$ in these formulae (I)/(II) is preferably the radical, reduced by the glycidyl groups, of a polyether, a polyether polyol, a polyester or a polyester polyol;

of a hydrocarbon radical which can have a saturated or unsaturated aliphatic character and/or aromatic character and which can be interrupted by hetero atoms, such as oxygen and nitrogen, and by hetero atom groups, such as —$NR^1CO$— ($R^1$ has the same meaning as above) and/or can contain these, this hydrocarbon radical as a rule containing at least 6, preferably at least 12 to 30, carbon atoms; these radicals are preferably aryl groups, in particular phenyl groups, which can be substituted, but are preferably unsubstituted; or of a reaction product of an epoxide compound with polyamines, polyols, polycaprolactone polyols, polyesters containing OH groups, polyethers, polyglycols, hydroxyl-, carboxyl- and amino-functional polymer oils, polycarboxylic acids or hydroxyl- or amino-functional polytetrahydrofurans. $R^4$ can also be various radicals of this type.

$R^4$ in particular is the corresponding radical of a bisphenol A diglycidyl ether, of a bisphenol F diglycidyl ether or of an oligomer thereof, or of a diglycidyl ester of tetrahydrophthalic, phthalic, isophthalic or terephthalic acid or a mixture of these radicals.

$R^4$ can also be a polyglycidyl ether of phenol/formaldehyde or cresol/formaldehyde novolaks.

Some of these radicals $R^4$ are shown by way of their formulae below:

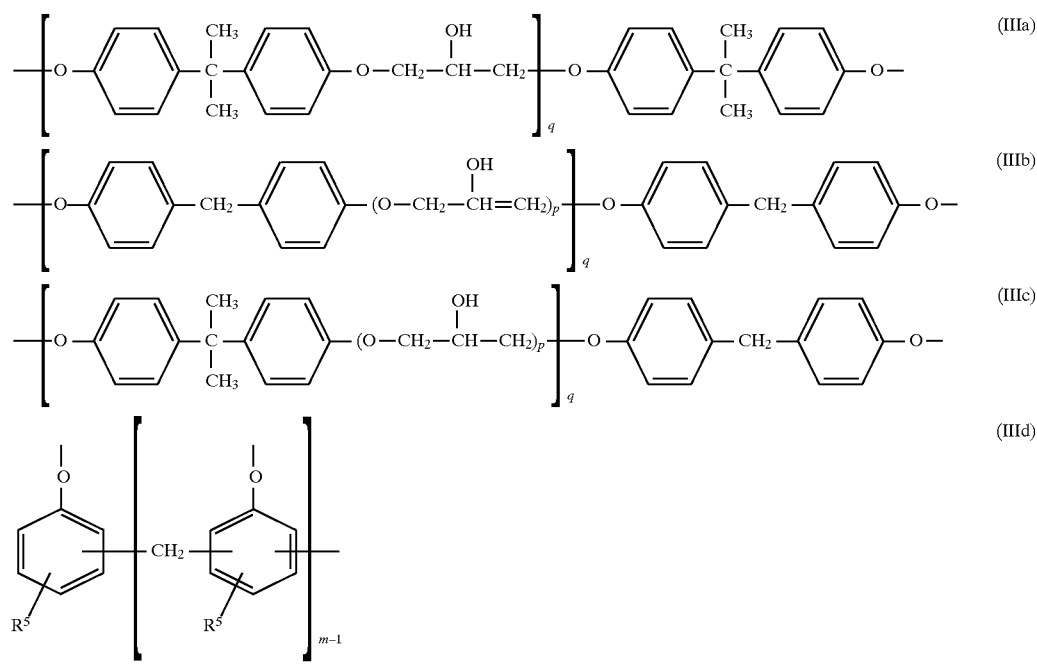

in which the index m has the above meaning, q is an integer from 0 to 40, preferably 0 to 10, the index p is 0 or 1 and $R^5$ is hydrogen and/or a $C_1$- to $C_{10}$-alkyl radical.

$R^4$ especially is (IIIa), i.e. the particularly preferred phosphorus-modified epoxy resins have the formulae (I') and (II'):

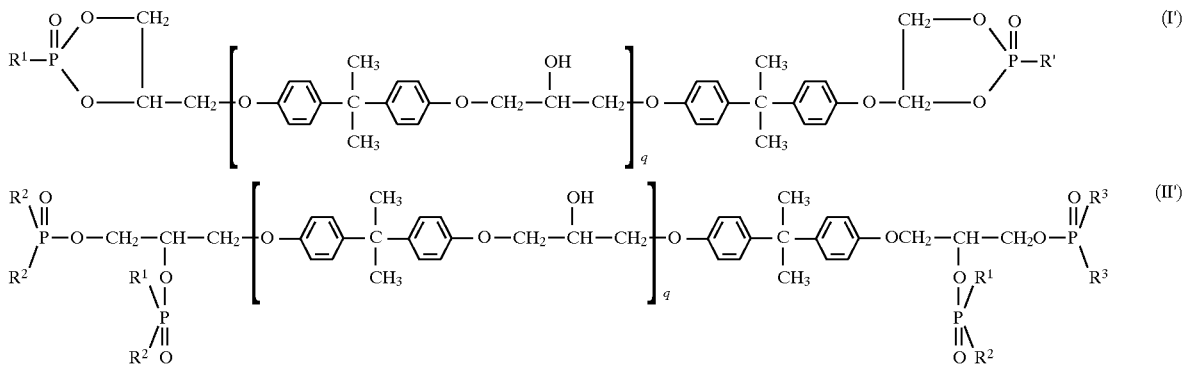

The phosphorus-modified epoxy resins according to the invention can also comprise certain amounts, usually not more than 30% by weight, preferably not more than 20% by weight, based on the total mixture, of other structural units, depending on the preparation method and the purity of the phosphonic acid/phosphinic acid anhydrides employed. Such by-products in the stated amounts do not substantially influence the profile of characteristics of the products according to the invention; in general, they even contribute toward the flame retardant action.

As already mentioned above, the phosphorus-modified epoxy resins according to the invention are particularly distinguished by a good storage stability.

The storage stability, expressed by the change in the epoxide value after 96 hours at room temperature and a relative atmospheric humidity of not more than 50%, as a rule does not fall below the value of 90%, and preferably varies in the range from about 95% to 100%, based on the starting value of 100%. In some of the phosphorus-modified resins according to the invention, however, these values can be achieved only by admixing phosphorus-free epoxy resins of the following formula (VI), preferably the same resin which has been used for the preparation of the compounds according to the invention.

The phosphorus-modified epoxy resins according to the invention are expediently prepared by reaction of phosphonic acid anhydrides of the formula (IV) and/or phosphinic acid anhydrides of the formula (V)

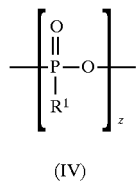    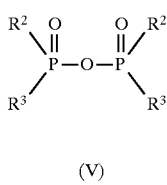

(IV)                     (V)

in which $R^1$, $R^2$ and $R^3$ have the abovementioned meaning and z is at least 3, preferably 3 to 10, and in particular 3, with polyepoxide compounds of the formula (VI)

    $R^4$        (VI)

in which $R^4$ and the index m likewise have the above meaning, in an inert solvent (diluent) or, with an adapted reaction procedure, also in bulk.

Possible phosphonic acid anhydrides of the formula (IV) are, for example: methanephosphonic anhydride, ethanephosphonic anhydride, n- and/or i-propanephosphonic anhydride, hexanephosphonic anhydride, benzenephosphonic anhydride and tolylphosphonic anhydride, or else corresponding mixtures.

The preparation of these phosphonic acid anhydrides is described, for example, in EP-A 0 004 323. Reference may furthermore also be made in this context to Houben-Weyl, Meth. d. Organ. Chem. [Methods of Organic Chemistry] (1963), Volume XII/1, page 612 and to DE-As 2 758 580 and 4 126 235.

Phosphinic acid anhydrides of the formula (V) which may be mentioned here are, for example: dimethylphosphinic anhydride, ethylmethylphosphinic anhydride, diethylphosphinic anhydride, dipropylphosphinic anhydride, methylphenylphosphinic anhydride, diphenylphosphinic anhydride, di-p-tolylphosphinic anhydride and di-p-methoxyphenylphosphinic anhydride.

The preparation of the phosphinic acid anhydrides is described, for example, in DE-A 2 129 583.

The anhydrides used according to the invention can comprise certain amounts of free acids, depending on their preparation method, but as a rule not more than 20% by weight, preferably not more than 15% by weight, and in particular not more than 10% by weight.

Polyepoxide compounds of the formula (VI) which are preferably employed are bisglycidyl ethers based on bisphenol A, bisphenol F and bisphenol S (reaction products of these bisphenols and epichloro(halogeno)hydrin) or oligomers thereof and diglycidyl esters of phthalic, isophthalic, terephthalic, tetrahydrophthalic and/or hexahydrophthalic acid. Further suitable polyepoxide compounds are described in "Handbook of Epoxy Resins" by Henry Lee and Kris Neville, McGraw-Hill Book Company, 1967, in the monograph by Henry Lee "Epoxy Resins", American Chemical Society, 1970, in Wagner/Sarx, "Lackkunstharze" [Synthetic Resins for Coatings], Carl Hanser Verlag (1971), page 174 et seq., in "Angew. Makromol. Chemie", Volume 44 (1975), pages 151 to 163, in DE-A 2 757 733, in EP-A 0 384 939 and in German Patent Application P 4 308 185.1; reference is made here to these literature sources.

If solvents (diluents) are employed in the process according to the invention, these are aprotic and preferably have a polar character. Examples of these are: N-methylpyrrolidone; dimethylformamide; ethers, such as diethyl ether, tetrahydrofuran, dioxane and ethylene glycol mono- or diethers, propylene glycol mono- or diethers and butylene glycol mono- or diethers of mono-alcohols having an optionally branched alkyl radical of 1 to 6 carbon atoms; ketones, such as, for example, acetone, methyl ethyl ketone, methyl isopropyl ketone, methyl isobutyl ketone, cyclohexanone and the like; esters, such as ethyl acetate, butyl acetate, ethylglycol acetate and methoxypropyl acetate; halogenated hydrocarbons; and (cyclo)aliphatic and/or aromatic hydrocarbons, such as hexane, heptane, cyclohexane, toluene and the various xylenes, as well as aromatic solvents in the boiling range from about 150° to 180° C. (higher-boiling mineral oil fractions, such as ®Solvesso). The solvents can be employed here individually or as a mixture.

The reaction of the glycidyl ethers of the formula (V) with the anhydrides is in general carried out at temperatures from −20° to 170° C., preferably 20° to 130° C.

The phosphorus-modified epoxy resins according to the invention can advantageously be used as flame retardant additives in many fields of use for the production of shaped articles, prepregs, coatings or laminates (composite materials), in particular for insulating purposes in electrical engineering. These phosphorus-modified resins here can also be employed as a mixture with phosphorus-free epoxy resins in amounts of up to 80% by weight, preferably up to 50% by weight. Hardeners which can be used are the known epoxy resin hardeners, such as have been described, for example, in DE-A 2 743 680 or EP-A 274 646. These materials are suitable, for example, for covering, coating and encasing electronic elements, for insulating electrical coils, and for the production of insulating components and composite materials having fibrous intercalation components, in particular laminates for printed circuit boards.

The invention is illustrated in more detail by examples below.

EXAMPLE 1

250 g of an epoxy resin prepared by reaction of 2 mol of epichlorohydrin with 1 mol of 2,2-bis(4-hydroxyphenyl) propane (bisphenol A) and having an epoxide equivalent weight of 180 to 192 (Beckopox EP 140, epoxy resin from Hoechst), were heated to 40° C. 281 g (1.32 mol) of propanephosphonic anhydride, 50% strength in ethyl acetate, were added dropwise in the course of 90 minutes.

The reaction was exothermic. The mixture was then subsequently stirred for one hour and thereafter kept under reflux for 16 hours.

Refractive index: $n_D^{20}$: 1.4950.

Viscosity (tested with a Höppler viscometer): 2566 mPa·s [25° C.].

EXAMPLE 2

50 g of an epoxy resin prepared by reaction of 2 mol of epichlorohydrin with 1 mol of 2,2-bis(4-hydroxyphenyl) propane (bisphenol A; epoxy resin D.E.R. 332 Dow Epoxy Resins) and 31.5 g (0.159 mol) of ethyl-methyl-phosphinic anhydride were stirred at −150° C. for 6 hours; a further 20 g (0.1 mol) of ethyl-methylphosphinic anhydride were then added and the mixture was stirred at 150° C. for a further 16 hours. After cooling, a 75% strength solution was prepared with ethyl acetate.

Refractive index: $n_D^{22}$: 1.4870.

Viscosity (tested with a Höppler viscometer): 80 mPa·s [25° C.].

EXAMPLE 3

Production of Prepregs a) 195 g of an epoxidized novolak (epoxide value: 0.56 mol/100 g), 65 g of a polyamine having an amine content of 9.35%, 0.7 g of 2-methylimidazole in 140 g of methyl ethyl ketone and 40 g of dimethylformamide were added to a solution of 150 g of the reaction product from Example 1 (P content of the resin matrix 3.1%). The polyamine was prepared by trimerization of a mixture of toluene 2,4-diisocyanate and toluene 2,6-diisocyanate and subsequent hydrolysis (to give a product having an $NH_2$ value of 9.35%).

b) Glass fabric (glass fabric type 7628, weight per unit area 197 g/m²) was impregnated continuously with the solution obtained according to a) by means of a laboratory impregnating unit, and was dried in a vertical drying unit at temperatures of 50° to 160° C. Prepregs produced in this way had a residual gelling time of 123 seconds, and were non-tacky and stable on storage at room temperature (at a maximum of 21° C. and maximum 50% relative atmospheric humidity).

EXAMPLE 4

Production and Testing of Laminates

Eight of the prepregs produced according to Example 3 were pressed in a press at 175° C. under 30 bar. The 1.6 mm thick laminate was removed from the press after 40 minutes and then after-heated at 200° C. for 2 hours. The laminate obtained in this manner had a Tg of 180° C. (DMTA) and an average burning time according to UL 94 V of 3.8 seconds, which corresponded to the classification V-0.

Thermosetting materials for electrical engineering must have a low combustibility. Flame resistance in accordance with UL 94V-0 is usually required for these materials. In this test, a test specimen is flamed vertically at the lower edge with a defined flame. The sum of the burning times of 10 tests may not exceed 50 seconds.

We claim:

1. A phosphorus-modified resin of the formula (I) or the formula (II), or a mixture thereof,

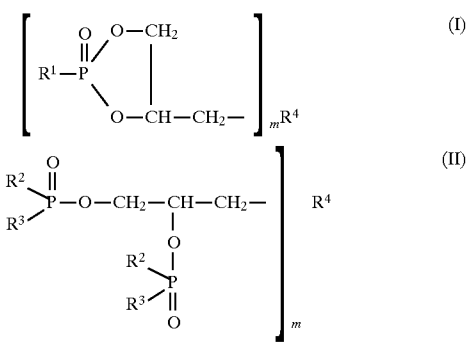

in which:

$R^1$, $R^2$ and $R^3$ independently of one another are each a hydrocarbon radical having 1 to 20 carbon atoms, $R^4$ is the radical of a glycidyl-group-containing polyepoxide from which the unreacted glycidyl groups have been eliminated, and m is a number from 2 to 6.

2. A phosphorus-modified resin as claimed in claim 1, in which $R^1$, $R^2$ and $R^3$ are each an aliphatic radical having 1 to 8 carbon atoms.

3. A phosphorus-modified resin as claimed in claim 1, wherein said resin is the reaction product of the components consisting essentially of a. a phosphonic acid anhydride and/or a phosphinic acid anhdyride, and b. at least one polyether, polyether polyol, polyester and/or polyester polyol diepoxide of the formula

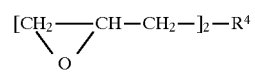

in which $R^4$ is the radical from the polyether, polyether polyol, polyester, and/or polyester polyol which remains in said reaction product after the two epoxide groups have been eliminated by the reaction of said components.

4. A phosphorus-modified resin as claimed in claim 1, which has an average molecular weight $\overline{M}_w$ ranging from 200 to 5,000.

5. An epoxy resin composition comprising a phosphorus-free epoxy resin and a phosphorus-modified resin as claimed in claim 1.

6. A process for the preparation of a phosphorus-modified resin as claimed in claim 1, which consists essentially of reacting a phosphonic acid anhydride of the formula (IV) and/or a phosphinic acid anhydride of the formula (V)

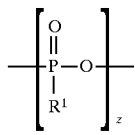  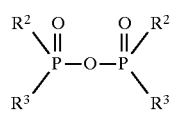

(IV)            (V)

in $R^1$, $R^2$ and $R^3$ are as defined in claim 1 and z is at least 3, with a polyepoxide of the formula (VI)

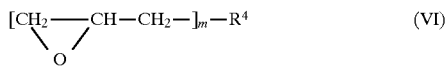

in which $R^4$ and m are as defined in claim 1, in an inert solvent or in bulk.

7. The process as claimed in claim 6, wherein the reacting step is carried out at a temperature ranging from −20° C. to 170° C.

8. The process as claimed in claim 6, wherein z of said formula IV is a number from 3 to 10.

9. A phosphorus-modified resin as claimed in claim 1, in which $R^4$ is the radical (IIIa):

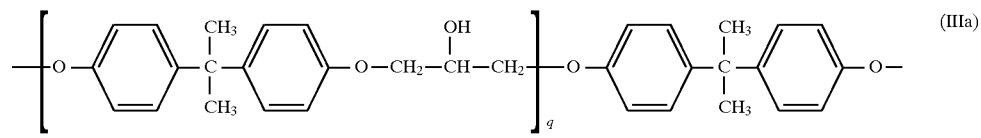

in which q is a number from 0 to 40.

10. A phosphorus-modified resin as claimed in claim 9, wherein q is a number from 0 to 10.

11. A phosphorus-modified resin as claimed in claim 1, wherein: m is a number from 2 to 4; and $R^1$, $R^2$ and $R^3$ are each an aliphatic radical having 1 to 4 carbon atoms.

12. A composite material containing a shaped portion, a preimpregnated portion, or layer or coating, which portion, layer or coating comprises a phosphorus-modified resin as claimed in claim 1 in combination with a phosphorus-free epoxy resin.

13. A method for making a composite material as claimed in claim 12, comprising the step of impregnating, laminating, or coating a material with said phosphorus-modified resin, in combination with a phosphorus-free epoxy resin.

14. A method as claimed in claim 13, wherein the combination of said phosphorus-modified resin and said phosphorus-free epoxy resin is hardened with an epoxy resin hardener.

15. An insulated electrical or electronic component wherein the insulation thereof comprises a composite material of claim 12.

16. A solution comprising a phosphorus-modified resin as claimed in claim 1 and a solvent therefor.

* * * * *